United States Patent
Atlas et al.

(10) Patent No.: US 11,540,765 B2
(45) Date of Patent: Jan. 3, 2023

(54) PULSATILITY MEASUREMENT AND MONITORING

(71) Applicants: Rutgers, The State University of New Jersey, New Brunswick, NJ (US); The Trustees of the Stevens Institute of Technology, Hoboken, NJ (US)

(72) Inventors: Glen Atlas, Livingston, NJ (US); Maria V. De Abreu Pineda, Hackensack, NJ (US); Andrew Falcone, Staten Island, NY (US); David J. Ferrara, Mount Arlington, NJ (US); Vikki Hazelwood, Wayne, NJ (US)

(73) Assignees: RUTGERS, THE STATE UNIVERSITY OF NEW JERSEY, New Brunswick, NJ (US); THE TRUSTEES OF THE STEVENS INSTITUTE OF TECHNOLOGY, Hoboken, NJ (US)

( * ) Notice: Subject to any disclaimer, the term of this patent is extended or adjusted under 35 U.S.C. 154(b) by 949 days.

(21) Appl. No.: 16/281,759

(22) Filed: Feb. 21, 2019

(65) Prior Publication Data
US 2019/0254584 A1    Aug. 22, 2019

Related U.S. Application Data

(60) Provisional application No. 62/633,915, filed on Feb. 22, 2018.

(51) Int. Cl.
A61B 5/024    (2006.01)
A61B 5/0295    (2006.01)
(Continued)

(52) U.S. Cl.
CPC .......... *A61B 5/4064* (2013.01); *A61B 5/0077* (2013.01); *A61B 5/0082* (2013.01); *A61B 5/0295* (2013.01); *A61B 5/02444* (2013.01); *A61B 5/4839* (2013.01); *A61B 5/7278* (2013.01); *A61B 5/7282* (2013.01); *A61B 5/742* (2013.01); *A61B 5/7405* (2013.01);
(Continued)

(58) Field of Classification Search
CPC ............................ A61B 5/0295; A61B 5/4064
See application file for complete search history.

(56) References Cited

U.S. PATENT DOCUMENTS

2009/0009615 A1    1/2009    Kennedy et al.
2011/0251493 A1    10/2011   Poh et al.

OTHER PUBLICATIONS

Wagshul et al., "The pulsating brain: A review of experimental and clinical studies of intracranial pulsatility" Fluids and Barriers of the CNS, vol. 8, article No. 5, 23 pages, (2011) (Year: 2011).*
(Continued)

*Primary Examiner* — Colin T. Sakamoto
(74) *Attorney, Agent, or Firm* — Michael Best & Friedrich LLP

(57) ABSTRACT

Systems and methods are presented for monitoring brain pulsatility. A change in volume of the brain is estimated based at least in part on an output of a non-contact, surface measuring sensor (e.g., a distance sensor or a camera). A metric indicative of brain pulsatility is then calculated based at least in part on a ratio of the estimated change in volume of the brain relative to a change in arterial blood pressure.

20 Claims, 3 Drawing Sheets

(51) Int. Cl.
A61B 5/00 (2006.01)
A61B 8/04 (2006.01)
A61B 5/021 (2006.01)

(52) U.S. Cl.
CPC ............... *A61B 5/746* (2013.01); *A61B 8/04* (2013.01); *A61B 5/021* (2013.01); *A61B 2505/05* (2013.01)

(56) References Cited

OTHER PUBLICATIONS

Behrens et al., "Transcranial Doppler pulsatility index: not an accurate method to assess intracranial pressure," Neurosurgery, 2010, 66:1050-1057.

Bouguetof et al., "Correlation between intracranial pressure and pulsatility index measured by transcranial Doppler in children with severe traumatic brain injury," Crit Care, 2015, 19 (Suppl 1):P449.

Cowan et al., "Changing Trends in the Use and Costs of Procedures Performed by Neurosurgeons in the United States," Clinical Neurosurgery, 2007, vol. 54, 209-11.

De Riva et al., "Transcranial Dopper pulsatility index: what it is and what it isn't," Neurocrit Care, 2012, 17:58-66.

Gobiet et al., "The relation between intracranial pressure, mean arterial pressure and cerebral blood flow in patients with severe head injury," Acta Neurochir, 1975, (Wien) 32(102):13-24.

Kern et al., "Spherical Segment," §36 in Solid Mensuration with Proofs, pp. 97-102, 1938.

Li et al., "Definition, evaluation, and management of brain relaxation during craniotomy," British Journal of Anaesthesia, 2016, 116 (6):759-69.

Marmarou et al., "Compartmental analysis of compliance and outflow resistance of the cerebrospinal fluid system," J Neurosurg, 1975, 43(5):523-34.

* cited by examiner

PULSATILITY MEASUREMENT AND MONITORING

RELATED APPLICATIONS

This application claims the benefit of U.S. Provisional Patent Application No. 62/633,915, filed Feb. 22, 2018, entitled "PULSATILITY MEASUREMENT AND MONITORING," the entire contents of which are incorporated by reference.

BACKGROUND

The present invention relates to systems and methods for monitoring physical and physiological conditions and changes of bodily organs. In particular, various embodiments of the present invention relate to system and methods for monitoring and mitigating conditions such as hypertension and hypotension of the brain during open-brain surgery—for example, during surgeries in which a craniotomy has been performed to access the brain.

During open-brain surgery, changes in the firmness (i.e., compliance) of the brain can be generally indicative of certain cerebral conditions of a patient. For example, changes in brain firmness can be indicative of adverse conditions that, if undetected, can cause irreversible brain damage in as little as 3 to 5 minutes.

SUMMARY

During some surgeries, a medical professional (e.g., a neurosurgeon or an anesthesiologist) may, for example, place one or more fingers on the brain to evaluate—based on touch—whether the brain appears more or less firm. However, this type of technique is subjective and can result in inaccurate determinations leading to complications during and after surgery. In particular, an erroneous assessment of brain compliance may result in over or under compensation of mitigating treatments (e.g., mannitol, hyperventilation), which may in turn result, for example, in cerebral ischemia, cerebral edema, and/or cardiovascular problems.

In various implementations, the invention provides methods and systems for monitoring and quantifying conditions of an organ such as, for example, pulsatility of the brain during open-brain surgery. In particular, some implementations provide systems for non-invasive and non-contact measurement of a quantifiable metric indicative of brain pulsatility. In various implementations, the system is further configured to output an indication of the measured brain pulsatility, generate an alarm output when the measured brain pulsatility is above or below one or more thresholds, and/or calculate an appropriate dosage of a medication based at least in part on the measured brain pulsatility.

In one embodiment, the invention provides a system for monitoring brain pulsatility including a non-contact, surface-measuring sensor and an electronic controller. The electronic controller is configured to estimate a change in volume of the brain based at least in part on an output of the surface measuring sensor. The electronic controller also receives a value indicative of a change in arterial blood pressure and calculates a metric indicative of brain pulsatility based at least in part on a ratio of the estimated change in volume of the brain relative to the change in arterial blood pressure Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
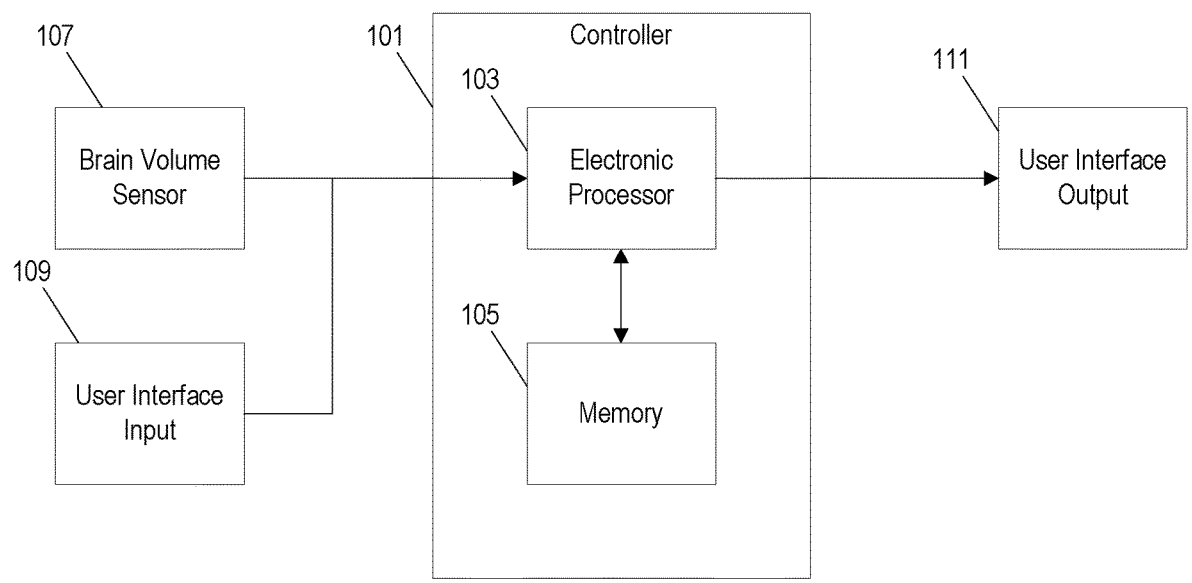
FIG. 1 is a block diagram of a system for measuring and monitoring brain pulsatility based on non-invasively detected changes in brain volume according to one embodiment.

FIG. 1 illustrates an example of a system for measuring brain pulsatility during open-brain surgery. The system includes a controller 101 with an electronic processor 103 and a non-transitory, computer-readable memory 105. The memory 105 is communicatively coupled to the electronical processor 103 and stores instructions that are executed by the electronic processor 103 to provide certain functionality of the controller 101 such as, for example, described herein. In some implementations, the memory 105 is also configured to store data including, for example, patient information, system configuration/calibration information, and look-up tables that may be used by the controller 101 to perform calculations relating to brain pulsatility and/or thresholds indicative of abnormal/adverse cerebral conditions.

The controller 101 is communicatively coupled to a brain volume sensor 107. The brain volume sensor 107 is configured to non-invasively collect information indicative of the volume of a patient's brain and/or changes in the volume of a patient's brain. For example, in some implementations, the brain volume sensor 107 includes an ultrasound system configured to measure a distance between the sensor 107 and a surface of the patient's brain. In other implementations, the brain volume sensor 107 may include other sensor technologies/modalities instead of or in addition to an ultrasound system including, for example, a video camera, a structured-light projector, a time-of-flight sensor, and a laser distance sensor (e.g., Lidar).

The controller 101 is also communicatively coupled to a user interface including a user interface input 109 and a user interface output 111. In some implementations, the user interface input 109 may include, for example, a keyboard and/or a pointing device such as a mouse or trackball while the user interface output 111 includes a display screen (e.g., an LCD display panel). In some implementations, the user interface input 109 and the user interface output 111 are provided as a single device or system including, for example, a touch-screen display, a tablet computer, a smart phone, or a laptop computer. In some implementations, the user interface output 111 may also include additional mechanisms for outputting information including, for example, one or more LED indicators or a speaker for emitting an audible tone. As discussed in further detail below, the system may be configured to output a "warning" signal in response to detecting potentially adverse cerebral conditions—this warning signal may, for example, cause one or more LEDs of the user interface output 111 to activate and/or flash and may cause the speaker of the user interface output 111 to emit an audible warning tone or other audible message.

The system of FIG. 1 is configured to measure brain pulsatility as a function of changes in brain volume. The volume of a healthy brain will pulsate as blood is pumped through the cerebral tissue by the heart. Accordingly, a degree to which the volume of the brain changes as it pulsates relative to the arterial blood pressure of the patient's cardiovascular system is indicative of brain compliance (e.g., firmness). Therefore, in some implementations, the system of FIG. 1 may be configured to measure brain pulsatility based at least in part on a ratio of a change in an observed brain volume relative to a change in mean arterial blood pressure. One example of an equation that might be used by the system of FIG. 1 to calculate brain pulsatility is:

$$\text{Pulsatility} = \frac{\Delta \text{ Cerebral Volume}}{\Delta \text{ Blood Pressure}} = \frac{\Delta V}{\Delta P} \quad (1)$$

In some implementations, such as in the example of FIG. 1, the system is simplified to include only a sensor 107 for capturing data indicative of changes in the volume of the patient's brain. The patient's blood pressure may be monitored, for example, using a cuff-based blood pressure monitor. The measured blood pressure is then periodically entered manually through the user interface input 109. The controller 101 will then perform a calculation to determine the measured brain pulsatility and generate an output signal based on the measured brain pulsatility. For example, as discussed in further detail below, the system may be configured such that the output signal causes the measured brain pulsatility value to be displayed on the user interface output 111 and, in some implementations, may cause the user interface output 111 to generate a visible or auditory alert in response to detecting a potentially adverse cerebral condition based on the measured brain pulsatility value.

In other implementations, the system may be configured to include additional sensors and/or to be in communication with additional systems. For example, in FIG. 2, the system again includes a controller 201 with an electronic processor 203 and memory, a brain volume sensor 207, a user interface input 209, and a user interface output 211. However, in the example of FIG. 2, the controller 201 is also in communication with an electronic arterial blood pressure sensor 213. The blood pressure sensor 213 may include, for example, an automated cuff-based system configured to periodically check blood pressure of the patient or another continuous non-invasive arterial pressure (CNAP) system for continuously measuring blood pressure of the patient. In various different embodiments, the blood pressure sensor 213 might continuously transmit to the controller 201 an output signal indicative of measured blood pressure (e.g., as a voltage input to an analog-to-digital converter of the controller 201) or a data packet including one or more calculated blood pressure values as determined by a separate controller or processor of the blood pressure sensor. The controller 201 is again configured to perform a calculation in order to determine a measured brain pulsatility. However, because the value indicative of blood pressure is received electronically from the blood pressure sensor, the system of FIG. 2 does not require blood pressure to be entered manually.

Figure 2:
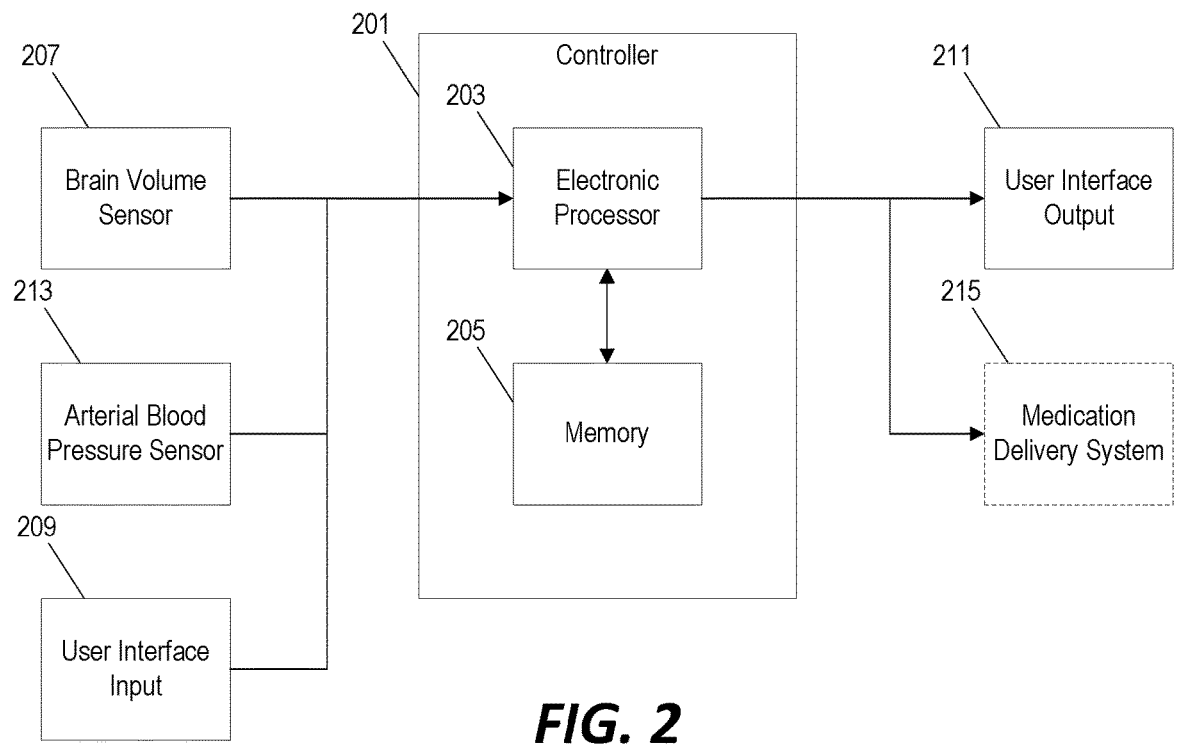
FIG. 2 is a block diagram of another system for measuring and monitoring brain pulsatility based on non-invasively detected changes in brain volume and an automated output of an arterial blood pressure sensors according to another embodiment.

Furthermore, as discussed above with reference to the system of FIG. 1, the system of FIG. 2 may also be configured to generate and transmit an output signal based on the measured brain pulsatility value which may cause certain information, instructions, or alerts to be output by the user interface output 211. However, the system of FIG. 2 may also be configured to include additional medical systems or to be in electronic communication with additional external medical systems. For example, as illustrated in FIG. 2, the controller 201 may be communicatively coupled to a medication delivery system 215 configured to provide a medication to the patient continuously at a defined rate or periodically at a defined interval. The system of FIG. 2 may, for example, be configured to calculate an appropriate dosage, rate, or interval for administering the medication based on the measured brain pulsatility and to transmit a signal or instruction to the medication delivery system 215 to cause the medication delivery system 215 to adjust the administered dosage of the medication. Alternatively, the system of FIG. 2 may be configured so that the controller 201 transmits the measured brain pulsatility value to the medication delivery system 215 and the medication delivery system 215 may be configured to automatically adjust the delivery of the medication based on the measured brain pulsatility value.

Figure 3B:
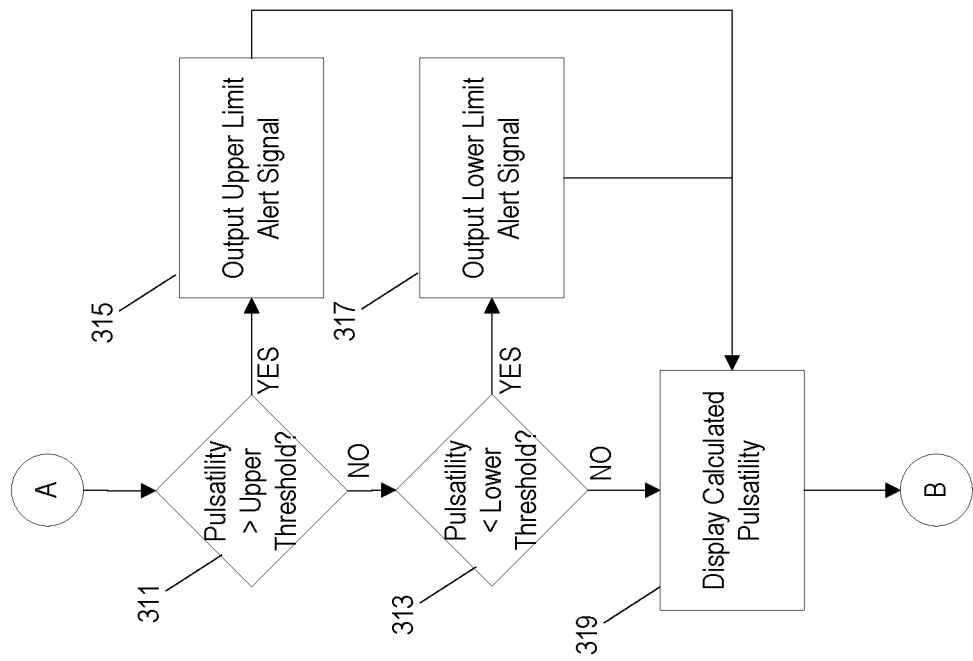
FIG. 3B is a flowchart of a method for generating an alarm output based on the brain pulsatility measured by the method of FIG. 3A.
Figure 3A:
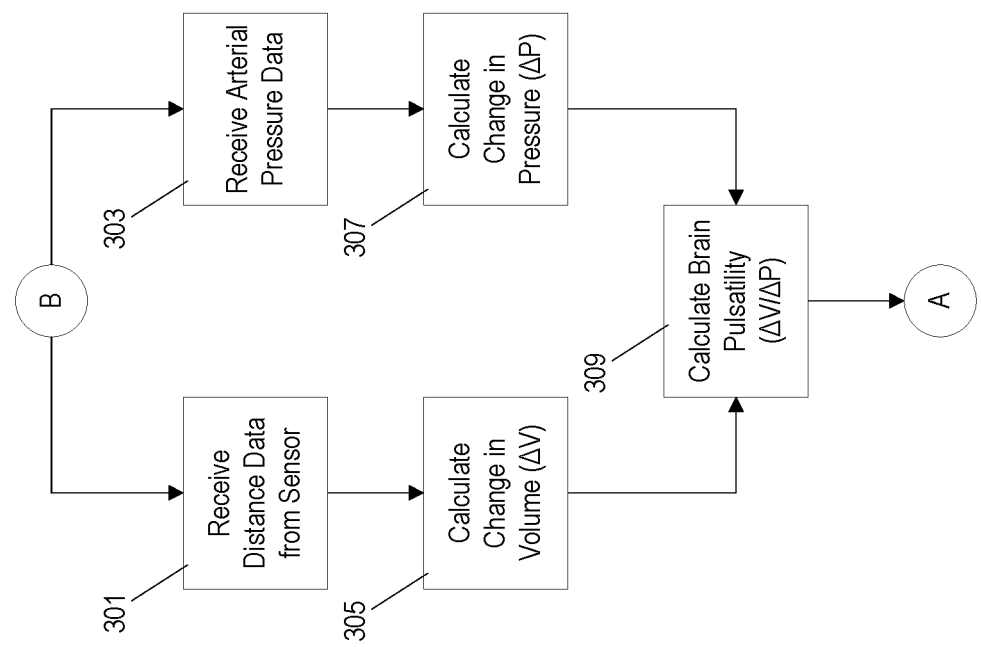
FIG. 3A is a flowchart of a method for measuring brain pulsatility using the system of FIG. 1 or FIG. 2.
Figure 3C:
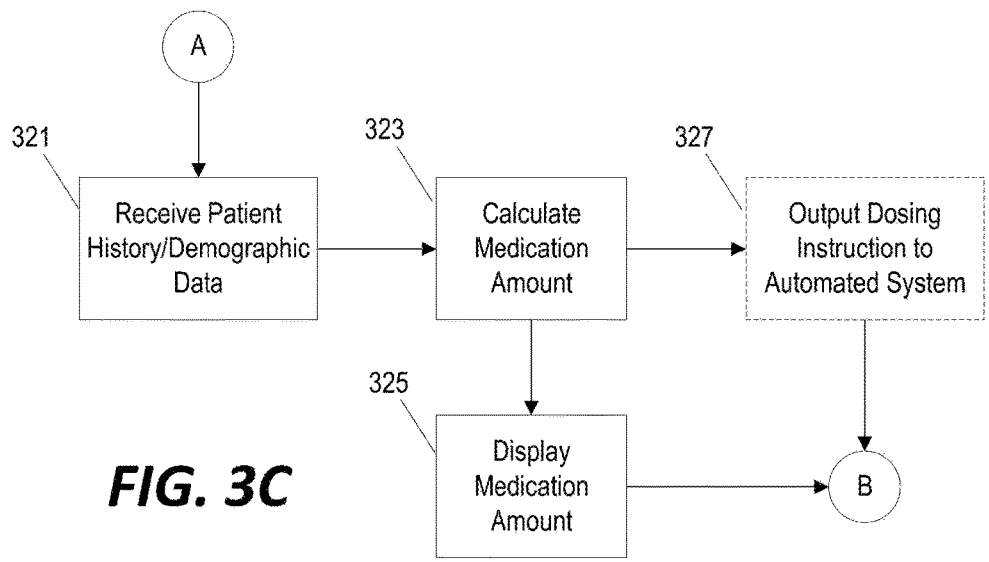
FIG. 3C is a flowchart of a method for administering a medication based on the brain pulsatility measured by the method of FIG. 3A.

FIGS. 3A, 3B, and 3C illustrate an example of a method for operating a system such as the system of FIG. 1 or the system of FIG. 2. It is noted that FIGS. 1 and 2 present just two examples of systems configured to measure brain pulsatility. Other implementations may include fewer, additional, or different components. Similarly, FIGS. 3A, 3B, and 3C also illustrate one particular example of operating a system such as the system of FIG. 1 or the system of FIG. 2. In other implementations, the operation of the system may include additional, fewer, or different steps.

In FIG. 3A, the controller receives a signal or data from the non-invasive brain volume sensor indicative of brain volume (step 301) and also receives arterial blood pressure data for the patient (step 303). Based on the output of the volume sensor, the controller calculates a change in the volume of the brain over a period of time (step 305) and, based on the received blood pressure data, the controller also calculates a change in blood pressure over the same period of time (step 307). Based on the change in brain volume and the change in blood pressure, the controller then calculates a value indicative of brain pulsatility, for example, using equation (1) (step 309).

The particular form in which the controller receives data from the sensor (i.e., in step 301) and the mechanism by which the controller calculates the change in brain volume (i.e., in step 305) may vary depending, for example, on the particular sensor used to monitor brain volume. For example, in some implementations, the brain volume sensor may include a distance sensor (e.g., an ultrasound sensor) configured to measure a distance between the sensor and a surface of the brain. The distance sensor may be configured to output a voltage that varies based on the measured distance. The output voltage of the distance sensor is coupled to the controller via an analog-to-digital converter, thereby enabling the electronic processor of the controller to monitor and record the distance values measured by the distance sensor.

In some implementations, the controller is configured to calculate the change in brain volume based on the output of the sensor using a technique such as, for example, the spherical cap model where the volume of the brain can be estimated by the equation:

$$V_{brain} \approx \frac{\pi h}{6}(3a^2 + h^2) \qquad (2)$$

where h is the distance or height to which the brain protrudes from the craniotomy and a is the radius of the craniotomy. In some implementations, the system may be configured to measure the values of h and a automatically (for example, using a combination of an ultrasound sensor and a digital camera). However, in some implementations, initial values of h and/or a might be manually entered into the system by a medical professional (e.g., the surgeon or the anesthesiologist). In implementations using a distance sensor (e.g., an ultrasound sensor as discussed above), changes in the distance measured by the distance sensor (i.e., the voltage output of the distance sensor) inversely correlate to changes in h—that is, the distance measured by the distance sensor between the sensor and the surface of the brain as the brain protrudes further from the craniotomy (i.e., as h increases).

Based on equation (2), changes in brain volume can be estimated by the system using the equation:

$$\Delta V \approx \frac{\pi}{2}(a^2 + h_i^2)\Delta h \qquad (3)$$

where $h_i$ is the initial value of h as defined by the user and $\Delta h$ is the change in h as determined based on the output of the ultrasound distance sensor. Furthermore, the system in some implementations may be configured to directly calculate the value of brain pulsatility after determining both a change in distance and a change in blood pressure using the equation:

$$\text{Pulsatility} = \frac{\Delta V}{\Delta P} \approx \frac{\pi}{2}(a^2 + h_i^2)\frac{\Delta h}{\Delta P} \qquad (4)$$

In some implementations, the method of FIG. 3A is repeated continuously or periodically to monitor changes in brain pulsatility throughout a surgical procedure. In some implementations, the system is also configured show the calculated value of brain pulsatility on a display of the user interface output as a number, a graph (showing changes in measured pulsatility over time), or both.

In some implementations, the system may be further configured to perform additional operations based on the brain pulsatility value calculated in step 309. For example, FIG. 3B illustrates an example of a method for generating alert signals in response to detecting potentially adverse conditions of the brain. After calculating the value of brain pulsatility (step 309), the controller compares the brain pulsatility value to an upper limit thresholds (step 311) and to a lower limit thresholds (step 313). The upper limit thresholds and lower limit thresholds in this example are defined based at least in part on brain pulsatility values indicative of intracranial hypertension and intracranial hypotension. In some implementations, the upper and lower limit thresholds are static thresholds defined for all users while, in other implementations, the upper and/or lower limit threshold may be determined dynamically based on patient information such as, for example, age, weight, medical history, etc. In some implementations, the controller receives the defined thresholds from an external system communicative coupled to the controller or by manual entry through the user interface input. In other implementations, the controller is configured to receive patient information (e.g., from a connected external system or manually through the user interface input) and then determines the threshold values. For example, the controller may be configured to use a "look-up table" stored to its memory to determine an appropriate threshold based at least in part on the received patient information while, in other implementations, the controller may be configured to calculate threshold values based at least in part on received patient information.

If the measured brain pulsatility value (as calculated in step 309) is above the upper limit threshold (step 311), then the controller generates and outputs an upper limit alert signal (step 315). Similarly, if the measured brain pulsatility value is less than the lower limit threshold (step 313), then the controller generates and outputs a lower limit alert signal (step 317). In various different implementations, these alert signal may be transmitted to an external system, may cause the system to activate a warning LED, may cause the system to display an alert message on a graphical user interface, and/or may cause the system to emit an audible alert tone through a speaker. Whether the measured brain pulsatility exceeds the upper limit threshold, falls below the lower limit threshold, or remains between the two thresholds, the controller causes the measured brain pulsatility value (as calculated in step 309) to be displayed on the display screen of the user interface output (step 319) and then continues to calculate subsequent brain pulsatility values (as set forth in FIG. 3A).

Furthermore, as mentioned above, the value of brain pulsatility calculated in step 309 can be used to determine an appropriate dosing of medication to be administered to a patient (e.g., mannitol). FIG. 3C illustrates an example of a method for this determination. After the value of brain pulsatility is calculated in step 309, the controller receives or accesses patient history and demographic information (e.g., age, weight, etc.) (step 321) and, based on the calculated brain pulsatility value and the accessed patient information, the controller calculates an appropriate medication amount, rate, or other dosing information (step 323). In some implementations, the appropriate dosing is determined, at least in part, using a look-up table stored on the memory of the controller. The medication dosing values stored in the look-up table can be determined experimentally based on observed conditions and/or defined based on input and review from anesthesiologists. In other implementations, the controller may be configured to determine an appropriate dosing based, at least in part, on one or more current or previous dosing amounts and previously detected changes in the brain pulsatility value corresponding to the previous dosing amounts. For example, in some implementations, the system may be configured to utilize a loop-based control mechanism such as, for example, a proportional-integral-derivative (PID) control to adjust a dosing amount based on observed feedback.

In some implementations, the controller causes the recommended medication dosing amount or rate to be displayed on the user interface output (step 325) where the suggestion can be viewed by an anesthesiologist. The anesthesiologist can then adjust the administration of the medication. Similarly, in some implementations, the controller can also be configured to output other instructions for mitigating potentially adverse brain conditions based on the measured value of brain pulsatility. For example, the controller in some implementations may be configured to display instructions for hyperventilation, fluid administration, the use of an epidural blood patch, and/or other techniques. Furthermore, in some implementations where the controller is in electronic communication with a medication delivery system (e.g., as illustrated in the example of FIG. 2), the medication dosing/amount as determined by the controller can then be electronically transmitted to the medication delivery system (step 327). The medication delivery system may be configured to adjust the automatic delivery of the medication based on the dosing/amount as determined by and received from the controller.

Again, the systems illustrated in FIGS. 1 and 2 and the methods illustrated in FIGS. 3A, 3B, and 3C are only examples of possible implementations. Other implementations are possible using other mechanism for calculating, estimating, and other measuring changes in brain volume using the sensors discussed above, other non-invasive sensors, or combinations of multiple non-invasive sensors. For example, instead of using an ultrasound sensor to measure changes in distance between the sensor and a surface of the brain, other sensors including, for example, a "time-of-flight" sensor or a laser-based distance sensor (e.g., Lidar).

Furthermore, in some implementations, a camera-based sensor can be configured to estimate changes in distance between the sensor and the surface of the brain either directly or using linear approximation. In some implementations employing a target tracking mechanism, a "marker" can be positioned on the surface of the brain or identified as a part of the external brain anatomy. For example, in some implementations, the system is configured to identify a particular sulcus at a location of the brain (e.g., near the center of the craniotomy) as the "target." As image data is repeatedly received from the camera, the controller identifies that "target" and calculates a size (e.g., a width) of the target in the image data. Because the apparent size of the target in the image data will increase as the target moves closer to the camera, the distance (and/or changes in the distance) between the camera/sensor and the surface of the brain can be calculated based on the apparent size of the target in the captured image data. The controller in some implementations is configured to then calculate an estimated change in brain volume based on the detected changes in distances, for example, using the spherical cap model as discussed above.

In other implementations, distance and/or volume of the brain can be calculated using image data from a camera using a grid overlay. For example, a grid pattern can be physically positioned on the surface of the brain or projected onto the surface of the brain by a light projector. As the brain pulsates, the apparent size of the grid relative to the camera will change and this change in the apparent size/shape of the grid pattern can be used by the controller to estimate a change in volume. Because the surface of the brain is not smooth—there are peaks and valleys (e.g., sulci)—using a grid overlay technique may provide a better determination of the actual width between the valleys, which may be a distinct "distance" independent from the surface. Furthermore, in some other implementations, instead of placing a physical grid or projecting a light-based grid on the surface of the brain, the controller may be configured to superimpose a "virtual" grid on image data of the brain captured by a camera.

Some implementations might also be configured to utilize transcranial Doppler (TCD) techniques. TCD is used to measure blood velocity and can be translated into two variables—arterial perfusion and "pulsatility index" (PI). However, in some implementations, a controller may be configured to utilize the variables measured by TCD to calculate an approximate change in the blood volume of a particular exposed section of the brain. Some such controllers are configured to determine a value of brain pulsatility based on the approximate change in blood volume relative to changes in mean arterial blood pressure.

Figure 4:
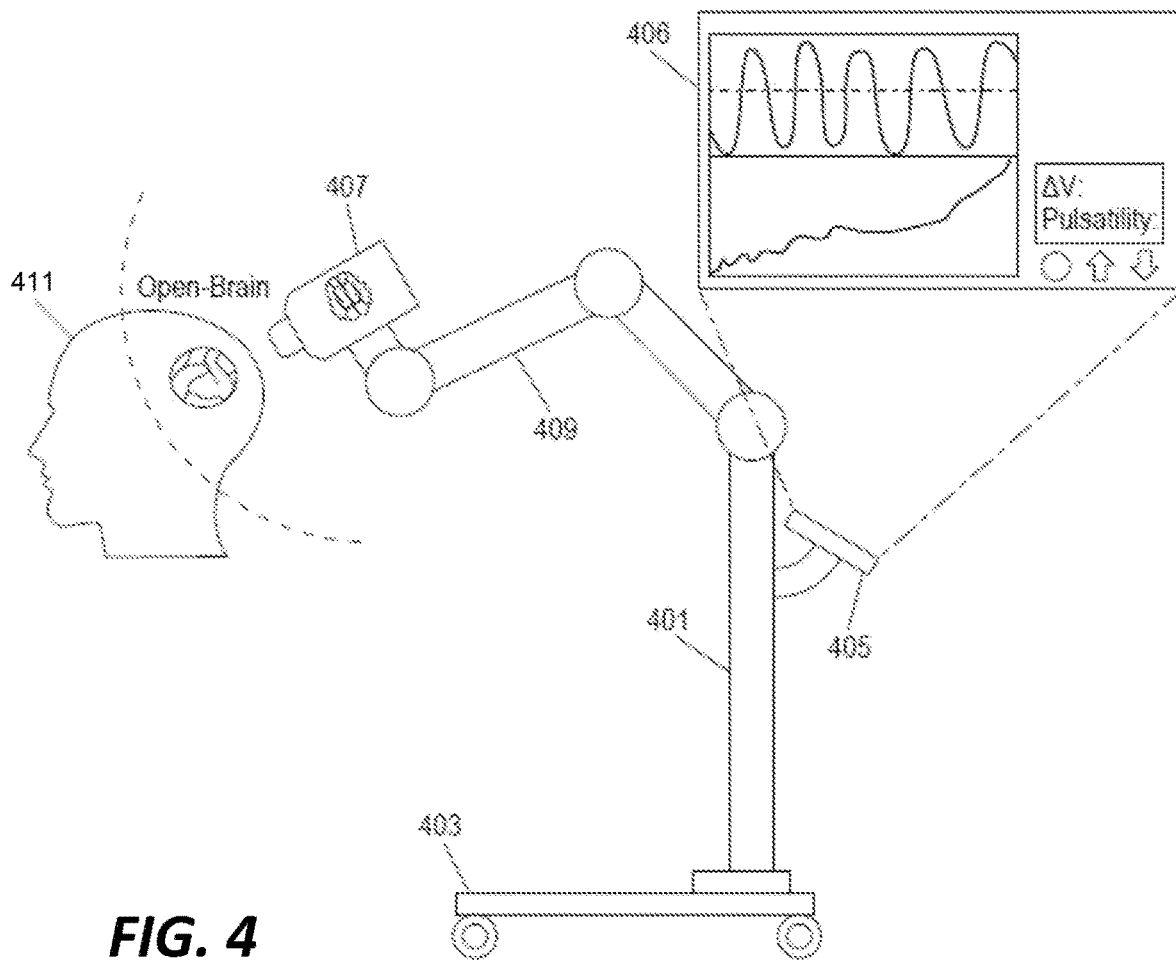
FIG. 4 is a schematic view of the system of FIG. 1 or FIG. 2 configured for portable use during surgical procedures.

FIG. 4 illustrates an example of a system for measuring and monitoring brain pulsatility configured for positioning during surgery. The system includes a central trunk 401 positioned on an easy-to-roll base 403 with wheels/casters. A user interface (e.g., a human-machine interface ("HMI") 405) is coupled to the central trunk 401 at a height viewable by a user (e.g., an anesthesiologist). In some implementations, the height and/or angle of the HMI 405 is selectively adjustable. As shown in the insert, the HMI 405 in the example of FIG. 4 includes a monitor 406 configured to display calculated/measured variables. In the example of FIG. 4, the monitor 406 is displaying (on the top graph) a graph of changes in brain volume over time and (on the bottom graph) the calculated pulsatility over the same period of time. A camera-sensor housing 407 is coupled to the central trunk 401 by a posable arm 409. The system of FIG. 4 is configured to be positioned near a surgical table and the camera-sensor housing 407 aimed at the open-brain of a patient 411 undergoing the surgical procedure. Coarse positioning adjustments of the camera-sensor housing 407 are made by moving the base 403 while fine-tuning adjustments can be made by adjusting the posable arm 409 and/or the angle of the camera-sensor 407 housing at the distal end of the posable arm 409.

Although the particular systems and methods described above may include specific arrangements and components, it is noted that other implementations may include additional, fewer, or different components and configurations. Similarly, although the examples discussed above relate to measuring a quantifiable metric indicative of brain pulsatility, in some other implementations, the system may be adapted to measure and monitor a quantifiable metric indicative of the pulsatility (and of other physical or physiological conditions and changes) of other bodily organs including, for example, the heart.

Thus, the invention provides, among other things, a system for measuring and monitoring a quantifiable metric indicative of pulsatility of a bodily organ including, for example, brain pulsatility. Various features and advantages of the invention are set forth in the following claims.

What is claimed is:

1. A system for monitoring brain pulsatility, the system comprising:
  a non-contact surface measuring sensor; and
  an electronic controller configured to
    estimate a change in volume of a brain based at least in part on an output of the surface measuring sensor,
    receive a value indicative of a change in arterial blood pressure, and
    calculate a metric indicative of brain pulsatility based at least in part on a ratio of the estimated change in volume of the brain relative to the change in arterial blood pressure.

2. The system of claim 1, wherein the surface measuring sensor includes a distance sensor, wherein the electronic controller is further configured to receive the output of the distance sensor indicative of a distance between the distance sensor and a surface of the brain.

3. The system of claim 2, wherein the distance sensor includes at least one selected from a group consisting of an ultrasound sensor, a laser distance sensor, and a time-of-flight light-based distance sensor.

4. The system of claim 2, wherein the electronic controller is further configured to
calculate an estimated volume of the brain based on the received signal from the distance sensor, and
wherein the electronic controller is configured to estimate the change in volume of the brain based at least in part on an output of the surface measuring sensor by comparing the estimated volume of the brain to a previous estimated volume of the brain calculated based on a previously received signal from the distance sensor.

5. The system of claim 2, wherein the electronic controller is configured to calculate the change in volume of the brain based at least in part on the output of the surface measuring sensor by calculating a change in volume of the brain using the equation:

$$\Delta V \approx \frac{\pi}{2}(a^2 + h_i^2)\Delta h$$

where $\Delta V$ is the change in volume of the brain, a is a radius of a craniotomy of a patient, $h_i$ is an initial height to which the surface of the brain protrudes from the craniotomy, and $\Delta h$ is a measured change in a height to which the surface of the brain protrudes from the craniotomy, and
wherein the electronic controller is configured to determine $\Delta h$ is based at least in part on the output of the distance sensor.

6. The system of claim 5, further comprising a user interface, wherein the electronic controller is configured to define the radius of the craniotomy a based at least in part on a user input received through the user interface.

7. The system of claim 5, further comprising a camera, wherein the electronic controller is configured to define the radius of the craniotomy a based at least in part on an image of the craniotomy captured by the camera.

8. The system of claim 2, wherein the distance sensor includes a camera.

9. The system of claim 1, wherein the electronic controller is further configured to:
compare the calculated metric indicative of brain pulsatility to an upper limit threshold, and
generate an alert signal in response to determining that the calculated metric indicative of brain pulsatility exceeds the upper limit threshold.

10. The system of claim 9, wherein the system is configured to activate an output in response to the alert signal generated by the electronic controller, wherein the output is selected from a group consisting of an audible output and a visual output.

11. The system of claim 1, wherein the electronic controller is further configured to:
compare the calculated metric indicative of brain pulsatility to a lower limit threshold, and
generate an alert signal in response to determining that the calculated metric indicative of brain pulsatility falls below the lower limit threshold.

12. The system of claim 1, wherein the electronic controller is further configured to determine a dosage of a medication based at least in part on the calculated metric indicative of brain pulsatility.

13. The system of claim 12, wherein the electronic controller is configured to determine the dosage of the medication based at least in part on a look-up table stored to a memory of the electronic controller defining a plurality of dosages each corresponding to at least one different metric indicative of brain pulsatility.

14. The system of claim 12, further comprising a user interface output display, wherein the electronic controller is configured to cause the determined dosage of the medication to be shown on the user interface output display.

15. The system of claim 1, further comprising a user interface output display, wherein the electronic controller is further configured to
select a mitigation technique based at least in part on the calculated metric indicative of brain pulsatility, and
cause the user interface output display to show an instruction for performing the mitigation technique.

16. The system of claim 15, wherein the mitigation technique includes at least one selected from a group consisting of a hyperventilation procedure, a fluid administration, and an epidural blood patch application.

17. The system of claim 1, further comprising a blood pressure monitor sensor, wherein the electronic controller is configured to receive the value indicative of a change in arterial blood pressure by receiving an output of the blood pressure monitor indicative of a current blood pressure value, and wherein the electronic controller is further configured to calculate a change in blood pressure based on the current blood pressure value received from the blood pressure monitor and at least one previous blood pressure value previously received by the electronic controller from the blood pressure monitor.

18. A method of monitoring brain pulsatility, the method comprising:
receiving, by an electronic controller from a non-contact surface measuring sensor, a signal indicative of a measurement of a surface of a brain;
calculating, by the electronic controller, an estimated change in volume of the brain based at least in part on the signal from the non-contact surface measuring sensor;
receiving, by the electronic controller, a value indicative of a change in arterial blood pressure; and
calculating a metric indicative of brain pulsatility based at least in part on a ratio of the estimated change in volume of the brain relative to the change in arterial blood pressure.

19. The method of claim 18, wherein receiving the signal indicative of the measurement of the surface of the brain includes receiving a signal indicative of a distance between the non-contact surface measuring sensor and the surface of the brain, and wherein the non-contact surface measuring sensor includes at least one selected from a group consisting of an ultrasound sensor, a laser distance sensor, a time-of-flight light-based distance sensor, and a camera.

20. The method of claim 18, further comprising:
comparing the calculated metric indicative of brain pulsatility to a defined threshold; and
automatically activating an alert signal based at least in part on the comparison.

* * * * *